(12) United States Patent
Spartiotis et al.

(10) Patent No.: US 9,772,410 B2
(45) Date of Patent: *Sep. 26, 2017

(54) SEMICONDUCTOR BUMP-BONDED X-RAY IMAGING DEVICE

(71) Applicant: OY AJAT LTD., Espoo (FI)

(72) Inventors: Konstantinos Spartiotis, Espoo (FI); Henri Tapio Nykanen, Helsinki (FI); Limin Lin, Espoo (FI); Tuomas Heikki Elmeri Lahtinen, Vantaa (FI); Pasi Juhani Laukka, Espoo (FI)

(73) Assignee: OY AJAT LTD., Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 15/054,261

(22) Filed: Feb. 26, 2016

(65) Prior Publication Data

US 2016/0181306 A1    Jun. 23, 2016

Related U.S. Application Data

(63) Continuation of application No. 14/666,344, filed on Mar. 24, 2015, now Pat. No. 9,329,284, which is a continuation of application No. 14/224,594, filed on Mar. 25, 2014, now abandoned.

(51) Int. Cl.
   *H01L 27/146*   (2006.01)
   *G01T 1/24*     (2006.01)
   *H01L 31/028*   (2006.01)

(52) U.S. Cl.
   CPC ........ *G01T 1/247* (2013.01); *H01L 27/14634* (2013.01); *H01L 27/14636* (2013.01); *H01L 27/14659* (2013.01); *H01L 27/14661* (2013.01); *H01L 31/028* (2013.01)

(58) Field of Classification Search
   CPC .............. G01T 1/247; H01L 27/14634; H01L 27/14636; H01L 27/14659; H01L 27/14661
   See application file for complete search history.

(56) References Cited

U.S. PATENT DOCUMENTS

| 5,952,646 | A | 9/1999 | Spartiotis et al. |
| 6,818,545 | B2* | 11/2004 | Lee .......... H01L 24/05 257/E21.508 |
| 6,933,505 | B2 | 8/2005 | Vuorela |
| 7,095,116 | B1 | 8/2006 | Kelkar et al. |
| 8,296,940 | B2 | 10/2012 | Woychik et al. |
| 2001/0040290 | A1 | 11/2001 | Sakurai et al. |
| 2002/0052065 | A1 | 5/2002 | Ogura |

(Continued)

FOREIGN PATENT DOCUMENTS

| DE | 102008050838 | 10/2009 |
| EP | 1239514 | 9/2002 |

(Continued)

OTHER PUBLICATIONS

International Search Report, dated Jun. 10, 2015; Application No. PCT/EP2015/056112.
Micro packaging at Advacam.

*Primary Examiner* — Casey Bryant
(74) *Attorney, Agent, or Firm* — Young & Thompson (57) ABSTRACT

A high pixel density intraoral x-ray imaging sensor includes a direct conversion, fully depleted silicon detector bump bonded to a readout CMOS substrate by cu-pillar bump bonds.

20 Claims, 4 Drawing Sheets

(56) References Cited

U.S. PATENT DOCUMENTS

| | | | |
|---|---|---|---|
| 2003/0124832 A1 | 7/2003 | Tseng et al. | |
| 2003/0129822 A1 | 7/2003 | Lee et al. | |
| 2003/0155516 A1 | 8/2003 | Spartiotis et al. | |
| 2003/0211720 A1 | 11/2003 | Huang et al. | |
| 2004/0023433 A1* | 2/2004 | Erikson | B81B 7/0006 |
| | | | 438/106 |
| 2004/0056351 A1 | 3/2004 | Wu et al. | |
| 2004/0188851 A1 | 9/2004 | Takewaki et al. | |
| 2004/0195516 A1* | 10/2004 | Matthews | H01L 24/11 |
| | | | 250/370.13 |
| 2005/0090090 A1 | 4/2005 | Kim et al. | |
| 2005/0170634 A1 | 8/2005 | Lin | |
| 2005/0230783 A1 | 10/2005 | Lin | |
| 2005/0239277 A1 | 10/2005 | Mercer et al. | |
| 2006/0051954 A1 | 3/2006 | Lin et al. | |
| 2006/0166402 A1 | 7/2006 | Lim et al. | |
| 2006/0252245 A1 | 11/2006 | Ke et al. | |
| 2007/0141824 A1 | 6/2007 | Wang | |
| 2008/0254611 A1 | 10/2008 | Sterrett et al. | |
| 2008/0265169 A1* | 10/2008 | Spartiotis | G01T 1/17 |
| | | | 250/370.09 |
| 2008/0296761 A1 | 12/2008 | Lee et al. | |
| 2009/0057895 A1 | 3/2009 | Lin et al. | |
| 2010/0140760 A1 | 6/2010 | Tam et al. | |
| 2010/0230810 A1 | 9/2010 | Kang et al. | |
| 2010/0246150 A1 | 9/2010 | Wong et al. | |
| 2011/0003470 A1 | 1/2011 | Burgess et al. | |
| 2011/0049706 A1 | 3/2011 | Huang et al. | |
| 2011/0073900 A1 | 3/2011 | Sugizaki | |
| 2011/0165776 A1 | 7/2011 | Hsu et al. | |
| 2011/0215476 A1 | 9/2011 | Lee et al. | |
| 2011/0291275 A1 | 12/2011 | Lin et al. | |
| 2012/0007231 A1 | 1/2012 | Chang | |
| 2012/0295434 A1 | 11/2012 | Cho et al. | |
| 2012/0313262 A1 | 12/2012 | Suzuki | |
| 2013/0143366 A1 | 6/2013 | Tam et al. | |
| 2013/0270329 A1 | 10/2013 | Schulte | |
| 2014/0327101 A1 | 11/2014 | Mori et al. | |
| 2015/0279890 A1 | 10/2015 | Spartiotis et al. | |

FOREIGN PATENT DOCUMENTS

| | | |
|---|---|---|
| EP | 1387402 | 2/2004 |
| KR | 20070036531 | 4/2007 |
| WO | 03-077319 | 9/2003 |
| WO | 2009061282 | 5/2009 |

* cited by examiner

Fig. 5

SEMICONDUCTOR BUMP-BONDED X-RAY IMAGING DEVICE

TECHNICAL FIELD

The current invention relates to a direct conversion, semiconductor x-ray imaging device where the detector substrate is bump bonded to the readout substrate. X-rays (or other type of radiation) impinges upon the detector and electron-holes pairs are created inside the detector substrate (thus the term "direct conversion") in response to the absorbed energy. Under the influence of an electric field applied across the detector these electrons (holes) are transferred to charge collection electrodes. The charge collection electrodes are connected to corresponding readout electrodes on a readout substrate, which act as the input to a readout pixel on the readout substrate. The connection is made via bumps and the known flip-chip bonding technique.

BACKGROUND ART

The technique of bumping and flip-chip bonding is widespread in the manufacturing of direct conversion x-ray imaging devices. Typically the bumps are grown with electroplating or electroless on the readout substrate side at a wafer scale. Then the wafer is diced and flip-bonded to the detector substrate. The bumps can however be grown on both sides, i.e., on the readout and/or the detector substrate. Typical bump compositions found in imaging devices are PbSn, BiPbSn, BiSn, Au, AgSn, and In. Each has its advantages. Examples of bump-bonded semiconductor radiation imaging devices can be found in U.S. Pat. No. 5,952,646A and U.S. Pat. No. 6,933,505B2. In Nuclear Instruments and Methods in Physics Research Section A Vol 527 Issue 3, Spartiotis et al.: "A CdTe real time X-ray imaging sensor and system", a detailed embodiment of a CdTe x-ray imaging device is disclosed where the bumps are BiSn, grown on the CMOS. The pixel size is 100 µm (one hundred micrometers) and by way of example the bump size is approximately 25 µm (twenty five micrometers) while the bump is roughly spherical. After the bonding the bumps are squashed and the bump is more like an ellipsoid with post bonding height of about 15 µm (fifteen micrometers). In Nuclear Instruments and Methods in Physics Research Section A Vol 501 Issues 2-3, Spartiotis et al.: "A directly converting high-resolution intra-oral X-ray imaging sensor", an x-ray imaging sensor for intraoral imaging is disclosed. The readout substrate is again a CMOS and the detector is fully depleted Si. The pixel size in this case is 35 µm (thirty five micrometers). For so small pixel size the bumps are expected to be of the order 10 µm-15 µm and the post bonding height around 10 µm.

In other prior examples, the bumps are grown on both the readout substrate (CMOS) and the detector substrate (Si, CdTe, CdZnTe etc). In such examples one finds In bumps and/or Au studs.

The prior techniques in bump-bonded semiconductor imaging devices work and are efficient due to the relatively large pixel size. By large pixel size is meant pixel pitch of thirty five micrometers (35 µm) to two hundred micrometers (200 µm). At the low end (close to 35 µm) the above described bump bonding techniques suffer from severe limitations:

During bonding the spherical shape of the bump becomes ellipsoid and the bump is squashed and extends laterally. There is a high risk of shorting a bump with its neighboring bump(s).

The surface (active area) of the detector and the CMOS (readout substrate) can be several square cm, and the uniformity of the spherical bumps becomes critical. A non-uniformity of the spherical bump shape of ±3 µm becomes critical in a substrate size of 2 cm×1 cm or larger. The manufacturing ability gets even more compromised for small pixel sizes, i.e., for pixels of 35 µm or less. For such small pixels the spherical bumps need to be 15 µm or smaller and such bumps become increasingly difficult to manufacture over large areas with sufficient uniformity (±3 µm) using conventional electroplating or electroless technique.

For pixel sizes less than 35 µm, the spherical bumps need be of the order of 5 µm-15 µm and as mentioned above making such PbSn, BiSn, AgSn, In (etc) spherical (or almost spherical) bumps of such small size, becomes increasingly difficult, especially given the large area and uniformity constraints.

The current bumps and interconnect technologies in semiconductor direct conversion radiation imaging devices have a deforming structure. This means that the whole bump or bonding element (which may have some other general shape as well) is deformed during the bonding process. As a result there is no "guaranteed" minimum post bonding height. The post bonding height depends on how much the bump (or bonding element) will be deformed, i.e., it depends on the bonding process, the bump size and bump uniformity across the readout substrate.

It is therefore no coincidence that the breakthrough intraoral sensor described in the above-cited NIM A501 2003 "A directly converting high-resolution intra-oral X-ray imaging sensor", never came to the market despite the efforts of several sensor manufacturers trying to employ the above mentioned conventional bump bonding techniques. The yield was too low and the manufacturing cost too high.

Furthermore, there are no known direct conversion, bump-bonded, high pixel density x-ray (or gamma ray, beta ray or other form of radiation) imaging devices, at least none produced regularly and with high yield. High pixel density means a readout pixel with size of less than sixty micrometers (<60 µm) and preferably less than thirty five micrometers (<35 µm) bump bonded to a detector pixel with size of less than thirty five micrometers (<35 µm).

DISCLOSURE OF INVENTION

The object of the current invention is to provide a direct conversion radiation imaging device that has reliable bonds even with small pixel sizes. Specifically, in accordance with the current invention, the direct conversion x-ray comprises a semiconductor detector substrate, a readout substrate and the two are bump bonded together with each detector pixel bonded to one or more readout pixels by means of bump bonds with rigid pillar elements.

A bump according to an embodiment has essentially a substantially rigid portion, usually of the element copper (Cu) or other metals such as Nickel (Ni), Aluminum (Al) etc., with high melting point and a bump solder "hat" grown on top of the rigid element. The bump solder hat has initially, during the manufacturing process, a semi spherical shape and is usual made from one of: tin (Sn), lead-tin (PbSn), bismuth-tin (BiSn), silver-tin (AgSn) etc. In the manufactured imaging device, the bump solder hat has a final cross-section shape of a compressed spherical shape, with upper and lower surfaces that are generally flat and parallel, and arcuate end surfaces connecting the upper and lower surfaces. The final shape of the bump solder hat may be a compressed ellipsoidal-like structure compressed along its minor axis, with upper and lower surfaces that are generally flat and parallel, and arcuate end surfaces connecting the upper and lower surfaces.

During the bonding process the temperature used is from 70° C. to 250° C. and the solder hat is in a reflow state or almost reflow state and is squeezed, just as an ordinary bump, found in the prior art, would be squeezed. However, the cu-pillary element (in the form typically of cylindrical or other type/shape of pillar) stays rigid and acts as a pillar that will not allow the two substrates, i.e., the detector and readout, to come closer than the height of the pillar. In this way the semiconductor direct conversion imaging device has a well-defined post bonding height, the solder hats are not shorted with each other or with the readout pixels and can be reliably manufactured even for the smallest pixel sizes, i.e., for pixels less than sixty micrometers (<60 µm), even less than thirty five micrometers (<35 µm) and even less than or equal to twenty five micrometers (<25 µm).

Figure 3:
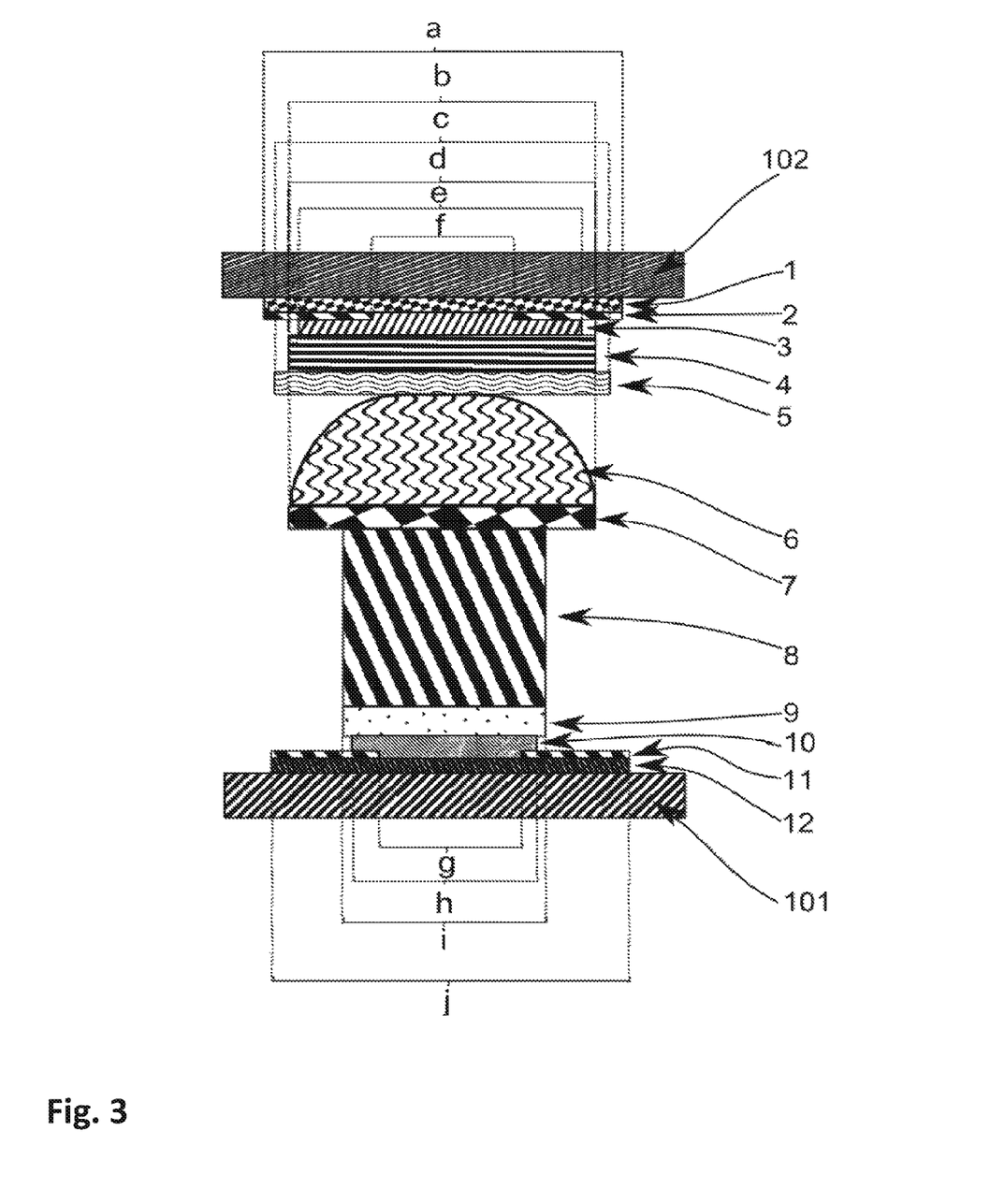
FIG. 3 shows a pillar with a solder hat on a readout pixel in accordance with an embodiment of the current invention and bonded to a detector substrate
Figure 4:
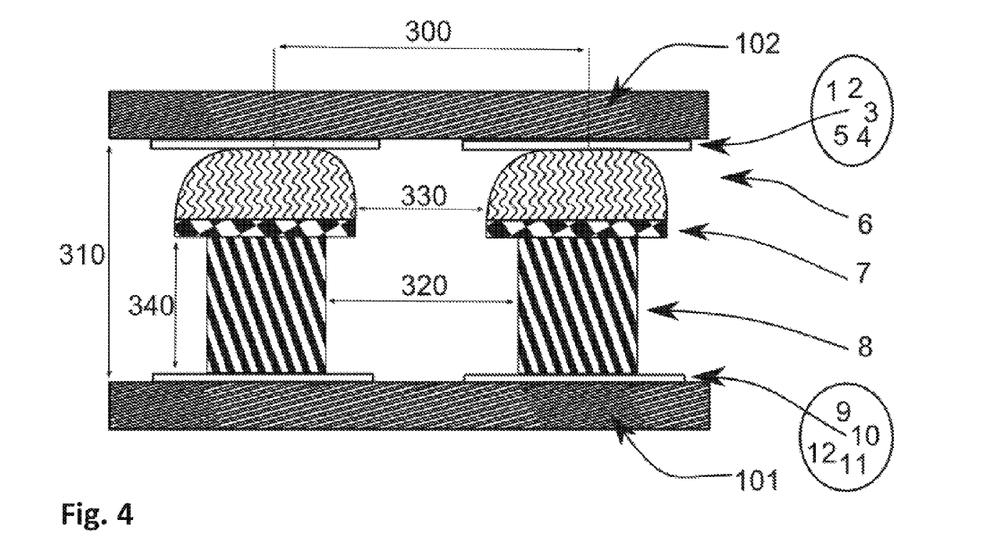
FIG. 4 shows an imaging device in accordance with an embodiment of the current invention.

In the present document, the term cu-pillary bump bond refers to a bump bond that has at least one copper pillary portion that has the general shape of a pillar, for example approximately a cylinder made of copper. The aspect ratio of the pillar is for example such that a height of the pillar is greater that its general width. However as may be deemed necessary in an application, the aspect ratio may also be such that the height is the same or smaller than its general width. The height refers herein to the direction from the first bonded element to the second element and the width is a dimension perpendicular to the height. In FIGS. 1-5, height is from element 101 to element 102. In FIG. 4, height is co-directional with arrows 310 and 340, and there is at least one width co-directional with arrows 320 and 330.

MODES FOR CARRYING OUT THE INVENTION

Figure 1:
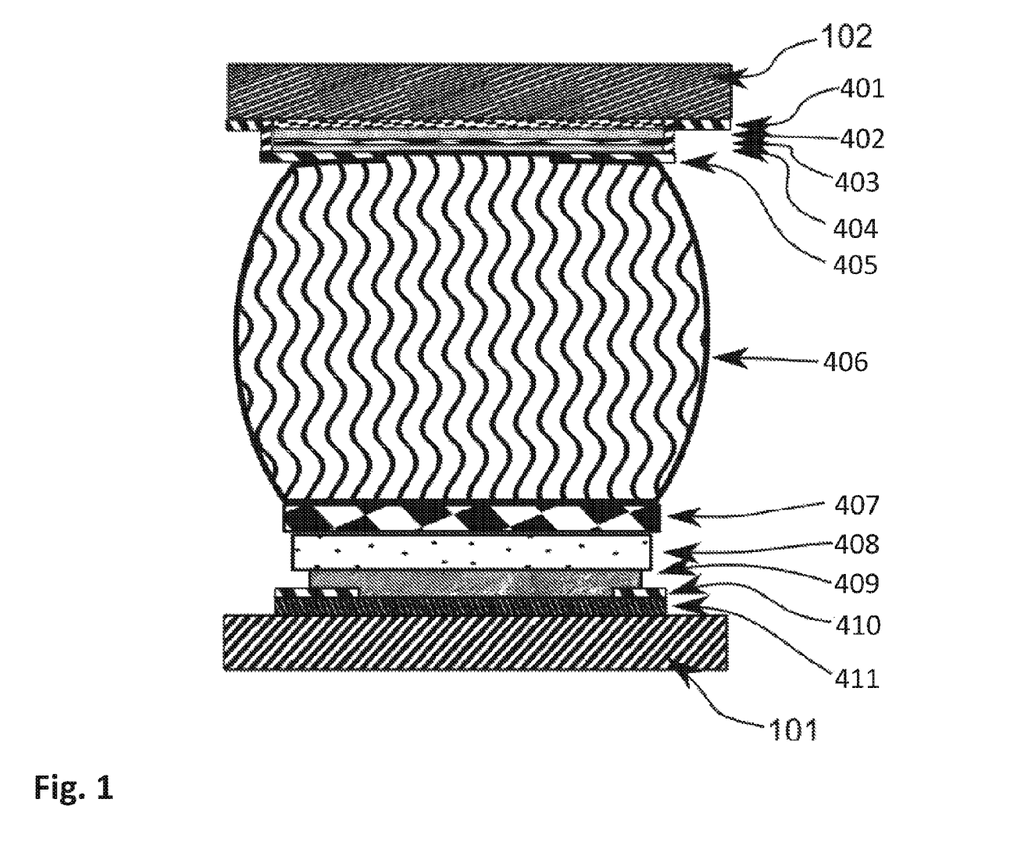
FIG. 1 presents a bump structure on a readout substrate.

With reference to FIG. 1, an imaging device, which can be made using previously known technology, is shown where a CMOS pixel 101 is bump-bonded to the corresponding detector pixel 102 via bump 406. A bump 406 is seen on a semiconductor readout pixel 101 (e.g., a CMOS). The bump 406 is of spherical shape. Under the bump one or more seed metal layers have been deposited. Typically, the seed layers are grown on the CMOS readout wafer 101 via sputtering or evaporation technique. Such a bump-bonded imaging device is shown in FIG. 1 and Table 1 all the elements are described with like numbers in the table below, indicating also the average thickness:

TABLE 1

| Name | Number | Material | Thickness (µm) (example average) |
|---|---|---|---|
| Detector pad | 401 | Pt (Platinum) | 0,050 |
| UBM 1 | 402 | Au (Gold) | 0,030 |
| UBM 2 | 403 | Ni (Nickel) | 0,050 |
| UBM 3 | 404 | Au (Gold) | 0,080 |
| Detector passivation | 405 | AlN (Aluminum Nitride) | 0,150 |
| Bump solder | 406 | SnBi (Tin Bismuth) | 10,000 |
| Bump pedestal | 407 | Ni (Nickel) | 1,600 |
| Bump seed bulk | 408 | Cu (Copper) | 0,500 |
| Bump seed adhesion | 409 | TiW (Titanium tangsten) | 0,040 |
| CMOS passivation | 410 | SiO2 (Silicon oxide) | 0,800 |
| CMOS pad | 411 | Al (Aluminum) | 1,200 |

The bump 406 need not be just SnBi, but can be composed by other types of solders like: PbSn, BiPbSn, AgSn, In, or other types of solder. The composition of the bump 406 is important in view of the bonding process. During the bonding process the CMOS readout substrate and the detector substrates are heated, then flipped and bonded together in accordance with a thermal-compression profile which defines the temperature ramp and pressure as a function of time. In some cases the bump is in a reflow state during bonding and in some other cases the bump is merely softened and compressed (for example with In). In radiation imaging the pixel sizes are typically in the range from few micrometers and up to one millimeter. The x-ray imaging devices pixel size where the flip-chip bonding technique is applied is in most cases in the range of 60 µm to 400 µm and most often the pixel size is in the range of 75 µm to 120 µm. The bumps in the prior art of bump bonded x-ray imaging devices are approximately of spherical shape or ellipsoid shape and with sizes typically in the range from 20 µm (in diameter) to 50 µm (diameter). Therefore the pre-bonding distance between the CMOS readout substrate and the detector is of the order of the size of the bump, i.e., between 20 µm and 50 µm.

Figure 2:
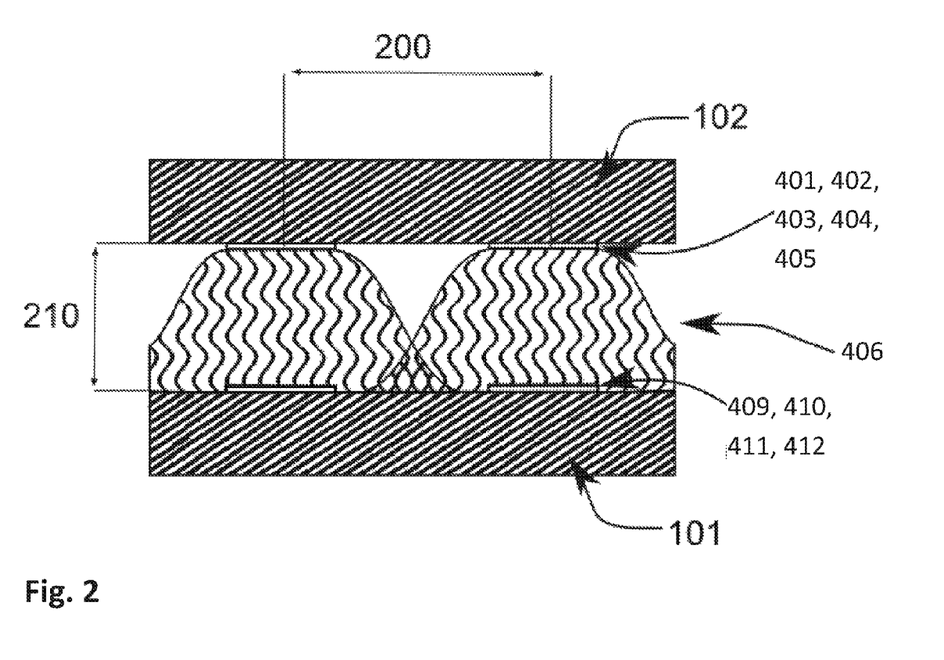
FIG. 2 shows an imaging device with the detector pixel bump bonded to the readout pixel, exemplifying the possible short-circuit issues with current bump-bonding technology.

FIG. 2 shows an end result of the bonding process with the bump of FIG. 1 in a problematic case. The bumps 406 have been deformed and the distance between the readout substrate and the detector substrate (post bonding height 210) is smaller or much smaller than the original bump height. For example for a bump height of 25 µm the post bonding height, i.e., the distance between the CMOS substrate 101 and the detector substrate 102 is typically 10 µm to about 15 µm. Simultaneously the bumps 406 have acquired an ellipsoid or asymmetrical shape and extend laterally approaching or exceeding the border of the bump in the next pixel. Even worse, "overwetting" may occur during the bonding reflow and the bumps on the CMOS side 101, flow towards one another and create short circuits as shown in FIG. 2. This may not really happen or be a problem when the pixel size (or pitch between the pixels) is of the order of 100 µm or larger (center to center distance 200 between the bumps), because there is enough distance to separate the bumps, even after they get squeezed. However, for small pixel sizes, i.e., for pixels less than 60 µm (i.e., it effectively means that the center to center distance 200 between the bumps) or even worse for pixel sizes of less than 35 µm, there is not enough or hardly enough separation between the bumps, post bonding. As an example, consider a 25 µm pixel size which is typical in intraoral x-ray imaging sensors. With such pixel size, the bump diameter would necessarily have to be approximately 15 µm. This would mean that the bump to bump separation 200 would be around 10 µm. After the bonding, the post bonding height 210 between the detector 102 and CMOS readout 101 would be 5 µm to no more than 10 µm, while the squeezed bumps would extend laterally and in many cases the separation 200 is eliminated at the CMOS side (as shown in FIG. 2) or on the detector side (not shown) and the imaging device has shorted bump connections. This results to loss of resolution and reliability issues.

Another important consideration is that the post bonding height 210 relates to the input node capacitance of the readout CMOS pixels. A bigger separation 210 between the detector and readout is desirable because it reduces the input node capacitance which means a better signal. The input node capacitance and the gain are related as is well known "V=Q/C", where (V) is the gain amplitude for a charge (Q) generated inside the detector substrate in response to incident radiation, with input node capacitance (C). With the traditional bump and bonding techniques the post bonding height is not controlled and can actually be quite small for small pixel sizes. Especially in an area of 3 cm×4 cm or 2 cm×3 cm, which is typical in x-ray imaging intraoral sensors, the post bonding height will vary between 5 µm and 10 µm as a result of parallelism inaccuracies between the two substrates. Therefore the input node capacitance will vary across the imaging device which is another down-side in addition to the risk of pixels been shorted with one another.

Finally, trying to control the post bonding height 210 within the range of 5 µm to 10 µm, brings manufacturing close to the limits (the accuracy) of available bonding equipment. With reference to FIG. 3, an embodiment of the invention is illustrated. A semiconductor Application Specific Integrated Circuit (ASIC) readout substrate, preferably a CMOS 101, is bump bonded to a direct conversion detector substrate 102 by means of a cu-pillary bump comprising a rigid bump leg 8 and a bump solder hat 6 positioned on top of the bump leg 8, preferably grown on the CMOS wafer prior to dicing. Thus, the bump legs 8 form the rigid portions of the bump bond in these embodiments. Ordinarily the CMOS wafers 101 are manufactured with a circular Al pad 12 (with diameter "j") at the input of the readout pixel. On the top of the Al pad 12, the CMOS manufacturer will ordinarily have deposited passivation layer $SiO_2$ 11. The passivation 11, has openings to the Al pad 12, said opening having a diameter "g". In an embodiment, then the following seed metals are deposited on top of the Al pad 12: TiW Bump Seed Adhesion layer 10 with inner diameter "h" and outer diameter "i", Cu Bump Seed Bulk metal 9 with diameter "i". These seed metals are typically deposited using sputtering technique. Following these seed metals, a Cu pillar (Bump Leg) 8 is grown using electroplating in the embodiment of FIG. 3. This can be made for example such that the pillars are grown in openings in a photoresist layer provided on the surface of the wafer, as is known in the art. Following the Cu pillar 8, the embodiment deposits a Ni Bump Pedestal layer 7 with diameter "b", also with electroplating. Following the Ni layer 7, the Bump Solder hat 6 is deposited. The Bump Solder hat 6 is preferably Sn, but can also be BiSn, PbSn, BiPbSn, AgSn or other solder types. As shown in FIGS. 3-4, the bump solder hat has a final cross-section shape of a compressed spherical shape, with upper and lower surfaces that are generally flat and parallel, and arcuate end surfaces connecting the upper and lower surfaces.

The detector material 102 for converting directly incoming x-ray radiation to electron-hole pairs is preferably fully depleted Si of thickness 0.5 mm to 2 mm. Alternatively, the detector material maybe CdTe or CdZnTe or GaAs. In the preferred embodiment of the current invention the detector is as mentioned Si, in single crystal form. Single crystal Si, fully depleted detector has the benefit of extreme uniformity and planarity and can be manufactured using conventional semiconductor industry's wafer level equipment. As a result very small pixel sizes can be achieved. For example in the preferred embodiment of the current invention an intraoral x-ray imaging sensor comprises Si fully depleted detector of thickness 0.5 mm to 2.0 mm with pixel size 25 µm or even smaller, e.g., 5 µm to 20 µm pixel size, such as 10 µm to 15 µm.

Always with reference to FIG. 3, the Si detector pixel 102 arrives from the factory with an Al Detector Pad 1 of diameter "a". Through this pad the signal from the direct conversion of x-ray to electron-hole pairs is collected (under the influence of an electric field). On top there is a Detector Passivation layer 2 which is most often $SiO_2$ and with an opening "f". In accordance with the embodiment, an Under Bump Metalization (UBM) adhesion layer 3 is next deposited, which is preferably TiW with outer diameter "e" and inner diameter "f". Then the UBM bulk layer 4 with diameter "d" is deposited, which is preferably Ni and then UBM solder pad which is preferably Au with diameter "c".

The CMOS readout pixel array 101 carries the cu-pillary bumps described above and is then flipped and bonded to the Si detector array with a corresponding number of detector pixels 102, as shown in FIG. 3. Table 2 below specifies example values of the dimensions and aspect ratios described above that the inventors have found are optimal to achieve a pixel to pixel distance of 25 µm. In other words the values in Table 2 have been optimized to achieve a pixel size of 25 µm in an intraoral Si x-ray imaging sensor. However, other parameter ranges can also be used in accordance with the embodiments. Further, the optimal ranges may differ from application to application and when the pixel size is different.

TABLE 2

| Name | Number | Material | Thickness (µm) EXAMPLE PREFERED EMBODIMENT |
|---|---|---|---|
| Detector pad | 1 | Al | 1,200 |
| Detector passivation | 2 | $SiO_2$ | 0,800 |
| UBM adhesion | 3 | TiW | 0,040 |
| UBM bulk | 4 | Ni | 0,340 |
| UBM solderpad | 5 | Au | 0,100 |
| Bump solder | 6 | Sn | 6,500 (from 4 to 7) |
| Bump pedestal | 7 | Ni | 1,600 (from 1 to 2) |
| Bump leg | 8 | Cu | 8,000 (from 5 to 12) |
| Bump seed bulk | 9 | Cu | 0,300 |
| Bump seed adhesion | 10 | TiW | 0,015 |
| ASIC/CMOS passivation | 11 | $SiO_2$ | 0,800 |
| ASIC/CMOS pad | 12 | Al | 1,200 |

| Name | Letter | Material | Width (µm) EXAMPLE PREFERED EMBODIMENT |
|---|---|---|---|
| Detector pad | a | Al | 15,000 (from 13 to 17) |
| Bump pedestal | b | Ni | 13,000 (from 12 to 16) |
| UBM solderpad | c | Au | 14,000 (from 13 to 17) |
| UBM bulk | d | Ni | 13,000 (from 12 to 16) |
| UBM adhesion | e | TiW | 12,000 (from 10 to 14) |
| UBM opening | f | — | 6,000 (from 4 to 8) |

TABLE 2-continued

| | | | |
|---|---|---|---|
| ASIC/CMOS Opening | g | — | 6,000 (from 4 to 8) |
| Bump seed adhesion | h | TiW | 10,000 (from 7 to 13) |
| Bump leg | i | Cu | 10,400 (from 7 to 13) |
| ASIC/CMOS pad | j | Al | 15,000 (from 12 to 18) |
| | k | — | — |
| | l | — | — |

According to another embodiment, the dimensions are within 20% to 150% of the nominal values indicated in Table 2. In another embodiment, the dimensions are within 50% to 125% of the values indicated in Table 2. In a further embodiment, the dimensions are within 75% to 110% of the values indicated in Table 2. In even further embodiments, the above-mentioned parameter ranges or their combinations apply otherwise but the thickness of the bump leg 8 layer is at least 4 μm, at least 5 μm or at least 6 μm.

In an embodiment, the cu-pillary bump comprises a bump leg 8 having a thickness (height) of 5-12 μm and a width i of 7-13 μm, and a plurality of other layers with their total thickness of at least 2 μm, such as 3-7 μm.

In an embodiment, the total height of the bump bond is greater than the general width (i) of the rigid portion of the bump bond.

FIG. 4 schematically shows a Si intraoral sensor cross section of two CMOS readout pixels 101 bump bonded by means of the disclosed cu-pillary bump bonds to their corresponding Si detector pixels 102. The center to center distance 300 of the cu-pillary bumps is 25 μm, which defines the pitch or pixel size. This is essentially the resolution of the final image to be displayed. The distance between the pillars 320 is also shown as well as the distance 330 between the solder hats 6. The post bonding height 310 in FIG. 4 is essentially the sum of the pillar leg 8 plus the solder hat 6 plus the bump pedestal 7, i.e., in the exemplified embodiment and with reference to Table 2 the post bonding height is of the order 8+6.5+1.6=16.1 μm, reduced by the amount the solder hats 6 have been squeezed. Therefore in practice the post bonding height 310 is between 10 μm to 15 μm. This distance is sufficient to keep the input node capacitance reasonably low. The current embodiments implement cu-pillary bump bonds in x-ray imaging devices and this is particularly beneficial when the center to center distance 300 between the bonds is 75 μm or less, while simultaneously the post bonding height 310 remains 5 μm or more. Preferably the center to center distance 300 between the bonds is 55 μm or less, while simultaneously the post bonding height 310 remains 8 μm or more. Even more preferably the center to center distance 300 between the bonds is 25 μm or less, while simultaneously the post bonding height 310 remains 8 μm or more.

Figure 5:
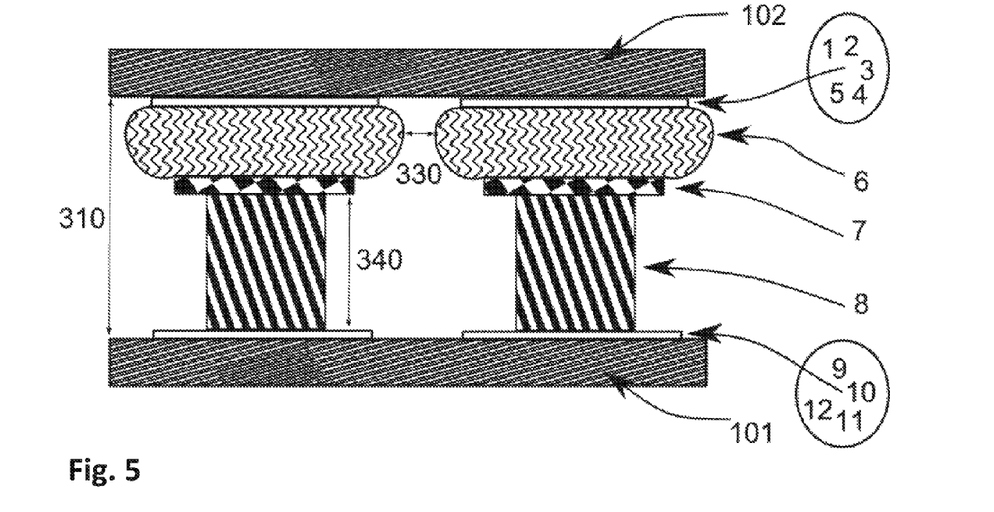
FIG. 5 shows an imaging device in accordance with an embodiment of the current invention, in which embodiment the post bonding height is minimum but still in excess of the pillar height (and no short circuits).

FIG. 5 shows, in a schematic way, the event of the effect of extreme pressure that may be applied during bump-bonding. The final shape of the bump solder hat is a compressed ellipsoidal-like structure compressed along its minor axis, with upper and lower surfaces that are generally flat and parallel, and arcuate end surfaces connecting the upper and lower surfaces. As can been seen the bump solder hats 6 have been severely deformed but still there is a sufficient clearance 330 between them. In other words, the short circuit of the pixels has been avoided unlike the situation of conventional bump bonded x-ray imaging device shown in FIG. 2. Also it can be seen that the pillar 8 and the solder bump pedestal 7 remaining essentially intact (rigid), regardless the fact that the solder hat has suffered severe deformation as a result of the bump-bonding. In other words with these embodiments one is able to control reliably the post bonding height 310. The lower limit of the post bonding height is the height of the pillar leg 8 plus the bump pedestal 7, i.e., 8+1.6=9.6 μm in this example. This feature is of a "guaranteed" post bonding height is beneficial for bump-bonding Si intraoral sensors because the detector substrate 102 and the readout substrate 101 are very large in area. Specifically, with the described embodiments, substrates of 1 cm×2 cm and up to 5 cm×5 cm can be reliably bonded with pixel sizes (interpixel pitch) that are 55 μm or smaller, 35 μm or smaller, 25 μm or smaller and even as small as 15 μm. The intraoral fully depleted Si x-ray imaging device is the preferred embodiment in this exemplified description.

The invention claimed is:

1. An x-ray imaging device comprising:
   a direct conversion detector substrate having detector pixels for collecting electronic signals generated in response to incident radiation;
   a readout substrate having readout pixels for receiving said electronic signals; and
   bump bonds connecting said detector pixels and readout pixels, each bump bond comprising a rigid pillar portion in the form of a rigid bump leg (8) and a bump pedestal layer (7) on the bump leg (8), the bump pedestal layer (7) having a width of 19.5 micrometers or less,
   wherein said detector pixels comprises an under bump metal bulk layer (4).

2. The x-ray imaging device of claim 1, wherein, said under bump metal bulk layer (4) has a diameter (d) in a range from 2.4 micrometers to 24 micrometers.

3. The x-ray imaging device of claim 2, wherein said under bump metal bulk layer (4) has a thickness in a range from 68 nanometers to 510 nanomenters.

4. The x-ray imaging device of claim 3, wherein said under bump metal bulk layer (4) comprises nickel (Ni).

5. The x-ray imaging device of claim 2, wherein said under bump metal bulk layer (4) comprises nickel (Ni).

6. The x-ray imaging device of claim 1, wherein said under bump metal bulk layer (4) has a thickness in a range from 68 nanometers to 510 nanomenters.

7. The x-ray imaging device of claim 6, wherein said under bump metal bulk layer (4) comprises nickel (Ni).

8. The x-ray imaging device of claim 1, wherein said under bump metal bulk layer (4) comprises nickel (Ni).

9. The x-ray imaging device of claim 1, wherein said rigid bump legs (8) have an average height of 5 micrometers or more, and said bump bonds further comprise bump solder hats (6) positioned on top of the rigid bump legs, an average post bonding height of the solder hats (6) being less than 6.5 micrometers.

10. An x-ray imaging device comprising:
    a direct conversion detector substrate having detector pixels for collecting electronic signals generated in response to incident radiation;
    a readout substrate having readout pixels for receiving said electronic signals; and
    bump bonds connecting said detector pixels and readout pixels, each bump bond comprising a rigid pillar portion in the form of a rigid bump leg (8) and a bump pedestal layer (7) on the bump leg (8), the bump pedestal layer (7) having a width of 19.5 micrometers or less,
    wherein said detector pixels comprise an under bump metal solderpad (5).

11. The x-ray imaging device of claim 10, wherein said under bump metal solderpad layer (5) has a diameter (c) in a range from 2.6 micrometers to 25.5 micrometers.

12. The x-ray imaging device of claim 11, wherein said under bump metal solderpad (5) has a thickness in a range from 20 nanometers to 150 nanometers.

13. The x-ray imaging device of claim 12, wherein said under bump metal solderpad (5) comprises gold (Au).

14. The x-ray imaging device of claim 13, wherein said rigid bump legs (8) have an average height of 5 micrometers or more, and said bump bonds further comprise bump solder hats (6) positioned on top of the rigid bump legs, an average post bonding height of the solder hats (6) being less than 6.5 micrometers.

15. The x-ray imaging device of claim 11, wherein said under bump metal solderpad (5) comprises gold (Au).

16. The x-ray imaging device of claim 11, wherein said rigid bump legs (8) have an average height of 5 micrometers or more, and said bump bonds further comprise bump solder hats (6) positioned on top of the rigid bump legs, an average post bonding height of the solder hats (6) being less than 6.5 micrometers.

17. The x-ray imaging device of claim 10, wherein said under bump metal solderpad (5) has a thickness in a range from 20 nanometers to 150 nanometers.

18. The x-ray imaging device of claim 17, wherein said rigid bump legs (8) have an average height of 5 micrometers or more, and said bump bonds further comprise bump solder hats (6) positioned on top of the rigid bump legs, an average post bonding height of the solder hats (6) being less than 6.5 micrometers.

19. The x-ray imaging device of claim 10, wherein said under bump metal solderpad (5) comprises gold (Au).

20. The x-ray imaging device of claim 10, wherein said rigid bump legs (8) have an average height of 5 micrometers or more, and said bump bonds further comprise bump solder hats (6) positioned on top of the rigid bump legs, an average post bonding height of the solder hats (6) being less than 6.5 micrometers.

* * * * *